United States Patent
Hoppe et al.

(10) Patent No.: US 8,857,662 B2
(45) Date of Patent: Oct. 14, 2014

(54) DISPENSERS AND FUNCTIONAL OPERATION AND TIMING CONTROL IMPROVEMENTS FOR DISPENSERS

(71) Applicants: Christopher S. Hoppe, Milwaukee, WI (US); Thomas P. Gasper, Germantown, WI (US); Bhaveshkumar Shah, Kenosha, WI (US)

(72) Inventors: Christopher S. Hoppe, Milwaukee, WI (US); Thomas P. Gasper, Germantown, WI (US); Bhaveshkumar Shah, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 13/858,607

(22) Filed: Apr. 8, 2013

(65) Prior Publication Data

US 2013/0240558 A1    Sep. 19, 2013

Related U.S. Application Data

(63) Continuation of application No. 12/915,427, filed on Oct. 29, 2010, now Pat. No. 8,464,905.

(51) Int. Cl.
 *B67B 7/00* (2006.01)
 *G01F 11/00* (2006.01)
 (Continued)

(52) U.S. Cl.
 CPC .............. *A61L 9/14* (2013.01); *A61L 2209/111* (2013.01); *A01M 1/2038* (2013.01); *A01M 1/026* (2013.01)
 USPC ................. 222/1; 222/52; 222/646; 222/649; 239/8; 239/69; 422/4; 422/123

(58) Field of Classification Search
 USPC ................. 222/1, 52, 63, 645, 646, 649, 333; 239/1, 8, 67–70; 422/4, 105–116, 422/120–126
 See application file for complete search history.

(56) References Cited

U.S. PATENT DOCUMENTS

| 3,610,471 A | 10/1971 | Werner |
| 4,184,612 A | 1/1980 | Freyre |

(Continued)

FOREIGN PATENT DOCUMENTS

| WO | 2004093929 A2 | 11/2004 |
| WO | 2008115391 A2 | 9/2008 |

(Continued)

OTHER PUBLICATIONS

PCT/US2011/001819 International Search Report dated Jul. 12, 2012.

*Primary Examiner* — Paul R Durand
*Assistant Examiner* — Matthew Lembo

(57) ABSTRACT

A method of operating a dispensing device includes the step of entering a first active state, in which the detection of sensory input by a sensor initiates a first pattern activation sequence to energize a drive unit of the dispensing device for a first length of time and a second subsequent length of time to actuate a container. Upon completion of the first pattern activation sequence, the device enters a second active state. The detection of sensory input in the second active state initiates a second pattern activation sequence to energize the drive unit for a third length of time and a fourth subsequent length of time to actuate a container if the sensory input is detected before a time period P lapses. The dispensing device initiates the first pattern activation sequence if the sensory input is detected after the lapsing of the time period P.

19 Claims, 4 Drawing Sheets

(51) Int. Cl.
*B67D 1/00* (2006.01)
*B67D 7/14* (2010.01)
*G04C 23/00* (2006.01)
*G05D 7/00* (2006.01)
*G04C 23/42* (2006.01)
*A01G 23/10* (2006.01)
*A01G 27/00* (2006.01)
*A61L 9/00* (2006.01)
*A62B 7/08* (2006.01)
*A01M 1/20* (2006.01)
*A61L 9/14* (2006.01)
*A01M 1/02* (2006.01)

(56) References Cited

U.S. PATENT DOCUMENTS

| | | |
|---|---|---|
| RE34,847 E | 2/1995 | Muderlak et al. |
| 6,026,987 A | 2/2000 | Burnett et al. |
| 6,529,446 B1 | 3/2003 | de la Huerga |
| 6,554,203 B2 | 4/2003 | Hess et al. |
| 6,610,254 B1 | 8/2003 | Furner et al. |
| 6,644,507 B2 | 11/2003 | Borut et al. |
| 6,672,129 B1 | 1/2004 | Frederickson et al. |
| 6,712,287 B1 * | 3/2004 | Le Pesant et al. ............... 239/67 |
| 6,739,479 B2 | 5/2004 | Contadini et al. |
| 6,790,408 B2 | 9/2004 | Whitby et al. |
| 6,877,636 B2 * | 4/2005 | Speckhart et al. ............... 222/1 |
| 6,948,192 B2 | 9/2005 | Hipponsteel |
| 7,188,485 B2 | 3/2007 | Szpekman |
| 7,398,013 B2 | 7/2008 | He et al. |
| 7,407,065 B2 | 8/2008 | Hooks et al. |
| 7,481,380 B2 | 1/2009 | Kvietok et al. |
| 7,622,073 B2 * | 11/2009 | Schramm et al. ............... 422/5 |
| 7,628,339 B2 | 12/2009 | Ivri et al. |
| 7,665,673 B2 * | 2/2010 | Hagleitner ............... 239/73 |
| 7,670,479 B2 | 3/2010 | Arett et al. |
| 7,673,820 B2 | 3/2010 | Ivri et al. |
| 7,735,694 B2 | 6/2010 | Brown et al. |
| 7,740,395 B2 | 6/2010 | Samuel et al. |
| 7,762,714 B2 | 7/2010 | Freeman et al. |
| 7,798,420 B2 | 9/2010 | Lind et al. |
| 7,832,655 B2 * | 11/2010 | Tollens et al. ............... 239/4 |
| 7,837,065 B2 | 11/2010 | Furner et al. |
| 8,061,562 B2 | 11/2011 | Carpenter et al. |
| 2004/0265164 A1 * | 12/2004 | Woo et al. ............... 422/5 |
| 2007/0199952 A1 | 8/2007 | Carpenter et al. |
| 2009/0045219 A1 | 2/2009 | Helf et al. |
| 2009/0117012 A1 | 5/2009 | Bankers et al. |
| 2009/0120962 A1 * | 5/2009 | Malorni et al. ............ 222/153.11 |
| 2009/0159719 A1 * | 6/2009 | Millet ............... 239/11 |
| 2009/0254770 A1 | 10/2009 | Sipinski et al. |
| 2009/0314849 A1 | 12/2009 | Litten-Brown et al. |
| 2010/0044468 A1 | 2/2010 | Granger et al. |
| 2010/0084418 A1 | 4/2010 | Reinsel et al. |
| 2010/0226818 A1 | 9/2010 | Miyagi et al. |
| 2010/0237108 A1 | 9/2010 | Anderson et al. |
| 2010/0243754 A1 | 9/2010 | Harris |
| 2010/0320227 A1 | 12/2010 | Reynolds |
| 2011/0295434 A1 * | 12/2011 | Luc et al. ............... 700/283 |

FOREIGN PATENT DOCUMENTS

| | | |
|---|---|---|
| WO | 2009151573 A2 | 12/2009 |
| WO | 2011056199 A1 | 5/2011 |

* cited by examiner

DISPENSERS AND FUNCTIONAL OPERATION AND TIMING CONTROL IMPROVEMENTS FOR DISPENSERS

CROSS REFERENCE TO RELATED APPLICATIONS

This application is a continuation application of U.S. patent application Ser. No. 12/915,427, filed Oct. 29, 2010.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to dispensers for discharging volatile materials and methods for operating the same, and more particularly to methods that increase user perception of the volatile materials and prevent habituation.

2. Description of the Background of the Invention

It is known that a user's perception of a dispensed fragrance of a constant intensity tends to decay over time. This decay in perception, which is commonly referred to as adaptation and/or habituation, increases as exposure to the fragrance is increased, eventually reaching a level of habituation wherein the consumer can no longer perceive the fragrance. It is generally believed that adaptation and/or habituation can be reduced by changing the level of intensity of the dispensed fragrance or by dispensing a different fragrance. Traditionally, fragrance habituation has been countered by step-wise increases in fragrance intensity. The drawback of this approach is that the consumer will repeatedly habituate to each increased level of fragrance intensity to reach a level of habituation wherein the fragrance can no longer be perceived.

Diffusion devices or dispensers are used to dispense volatile materials, such as fragrances, deodorizers, insecticides, insect repellants, and the like. Many such devices are passive diffusion devices that require only ambient air flow to dispense the volatile material, while other devices are active diffusion devices. Active diffusion devices are found in a variety of forms, some include fans and/or heaters to aid in the dispersal of volatile materials, others actuate a valve stem of an aerosol container to dispense a volatile material contained therein, still others utilize an ultrasonic transducer to break up a liquid volatile material into droplets that are ejected from the device, and yet others include any combination of the above or any other known type of active diffusion device. Further, some active diffusion devices include a sensor to detect motion or light in a space, wherein such devices dispense a volatile material in response to signals from the sensor.

Traditionally, fragrance dispensers that release fluid based on the detection of motion release the same spray burst after every detection of motion. The drawbacks of this approach are that the user will become habituated to the level of fragrance released and will not perceive the bursts of fragrance. Additionally, many of these dispensers release a spray burst after every detection of motion regardless of the last time the dispenser released a spray burst. The drawbacks of this approach are that in high-trafficked areas the dispenser releases many spray bursts, which, in addition to depleting the contents of the dispenser at a higher rate, cause the user to become habituated to the fragrance.

Consequently, a need has arisen for dispensers to provide an improved user experience by increasing user perception and preventing habituation by releasing fragrance using various patterned activation sequences. The present disclosure relates to solutions to address such needs.

SUMMARY OF THE INVENTION

According to one embodiment, a method of operating a dispensing device includes the step of entering a first active state, wherein if there is sensory input detected by a sensor of the dispensing device, the sensory input is detected and the dispensing device initiates a first pattern activation sequence that comprises the release of a volume A of material from a fluid container. Upon completion of the first pattern activation sequence, the device enters a second active state wherein if there is sensory input detected by a sensor of the dispensing device before the lapsing of a time period P, the sensory input is detected and the dispensing device initiates a second pattern activation sequence that comprises the release of a volume C of material from a container. Even further, in at least one of the first or second active states, (i) a volume B of material is released from the container subsequent to the release of the volume A or (ii) a volume D of material is released from the container subsequent to the release of volume C. The volume A, the volume B, the volume C, and the volume D are not all the same. Upon entering the second active state, if there is no sensory input detected by a sensor of the dispensing device before the lapsing of a time period P, the first pattern activation sequence is initiated.

According to a second embodiment, a method of operating a dispensing device includes the step of entering a first active state, wherein the detection of sensory input by a sensor initiates a first pattern activation sequence to energize a drive unit of the dispensing device for a first length of time and a second subsequent length of time to actuate a container. Upon completion of the first pattern activation sequence, the device enters a second active state wherein the detection of sensory input in the second active state initiates a second pattern activation sequence. The second pattern activation sequence energizes the drive unit for a third length of time and a fourth subsequent length of time to actuate a container if the sensory input is detected before a lapsing of a time period P. The dispensing device initiates the first pattern activation sequence if the sensory input is detected after the lapsing of the time period P.

According to a further embodiment, a method of operating a dispensing device includes the step of entering a first active state, wherein the detection of sensory input by a sensor initiates a first pattern activation sequence to energize a drive unit of the dispensing device for a first length of time to actuate a container. Further, the method includes the step of entering a second active state upon completion of the first pattern activation sequence. The detection of sensory input in the second active state initiates a second pattern activation sequence to energize the drive unit for a third length of time to actuate a container if the sensory input is detected before a lapsing of a time period P. The first pattern activation sequence is initiated if the sensory input is detected after the lapsing of the time period P. Even further, in at least one of the first and the second active states, (i) the drive unit is energized for a second length of time subsequent to the first length of time or (ii) the drive unit is energized for a fourth length of time subsequent to the third length of time.

Other aspects and advantages of the present invention will become apparent upon consideration of the following detailed description.

DETAILED DESCRIPTION OF THE DRAWINGS

Figure 1:
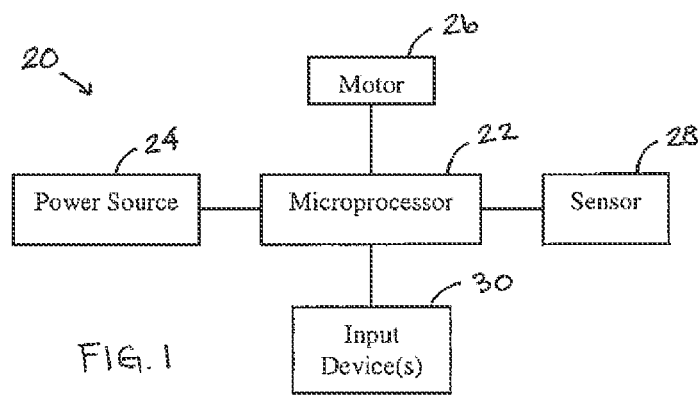
FIG. 1 is a block diagram of one embodiment of a dispenser.

FIG. 1 illustrates a device 20 that includes a microprocessor 22, a power source 24, a motor 26, and a sensor 28. The device may also include an input device 30. An example of the input device 30 may be a selector switch 32, which allows the user to turn on the device 20. The power source 24 supplies power to the microprocessor 22 and to the other components, wherein the microprocessor 22 is further coupled to the other components and executes programming to control the operation thereof. In one embodiment, the microprocessor 22 may be a Microchip PIC 18F2525. However, it is contemplated that any type of microcontroller known to those of skill in the art may be used with the present embodiments.

Figure 2:
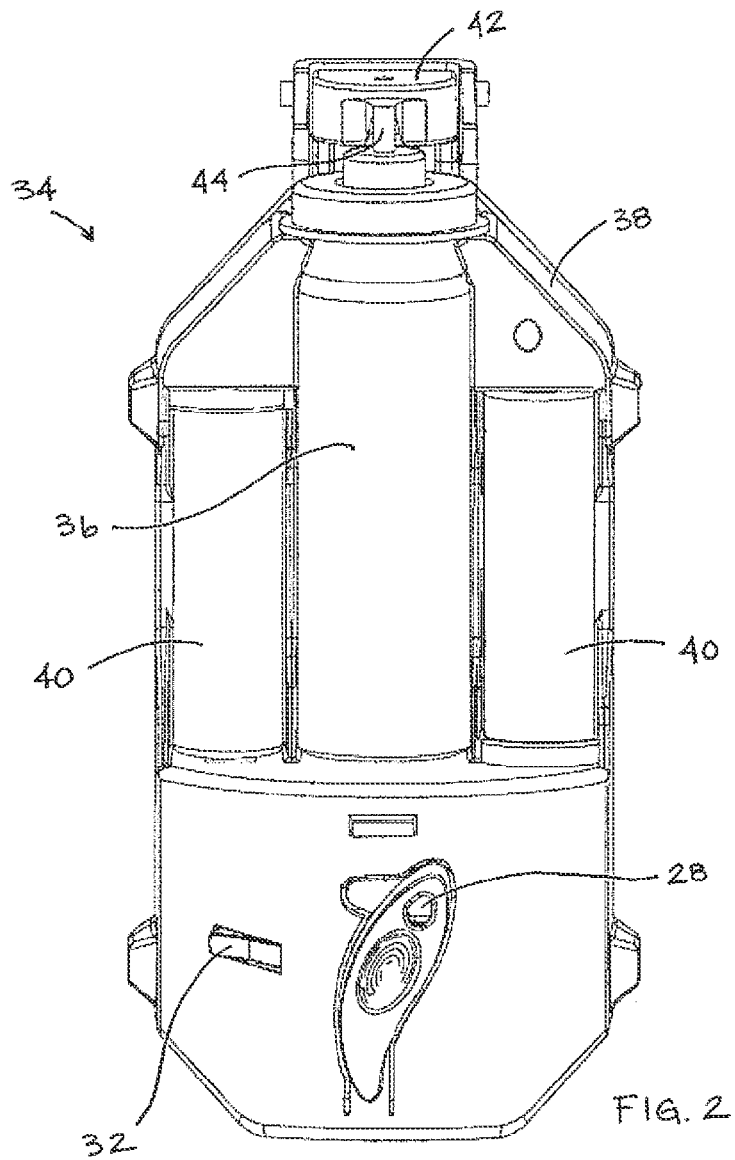
FIG. 2 is an isometric view of a dispenser according to another embodiment.

FIG. 2 illustrates an embodiment of the device 20 of FIG. 1 implemented as a dispenser 34 for dispensing the contents of an aerosol container 36. The dispenser 34 may be one of the devices described in Carpenter et al. U.S. patent application Ser. No. 11/725,402, which is incorporated herein by reference in its entirety. The dispenser 34 includes a housing 38 that is adapted to receive the aerosol container 36, batteries 40, actuator arm 42, and the selector switch 32. In addition, the dispenser 34 also includes circuitry, the microprocessor 22, the motor 26, and the sensor 28, which are provided within the housing 38 and shown generally in FIG. 1.

The microprocessor 22 controls the motor 26 during a spray release operation 50 to actuate the actuator arm 42, which depresses a valve stem 44 of the aerosol container 36 to dispense the contents therefrom. The microprocessor 22 includes programming to initiate a spray release operation 50 in response to a signal generated from the sensor 28. Alternatively, or in conjunction with the present embodiment, the microprocessor 22 could initiate a spray release operation 50 in response to a signal generated by a switch, a pushbutton, and/or a timer.

Figure 3:
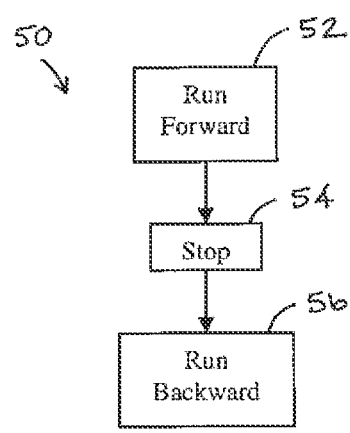
FIG. 3 is a flowchart that illustrates programming for a spray release operation that may be executed by the dispensers of FIGS. 1 and/or 2.

FIG. 3 illustrates the spray release operation 50 of the present embodiment. The spray release operation 50 begins at the block 52 where the motor 26 is energized to move the actuator arm 42 downwardly to depress the valve stem 44 of the aerosol container 36 into an open position. The motor 26 is deenergized in block 54. Thereafter, the motor 26 is energized to move the actuator arm 42 in the opposite direction in block 56 to assist the valve stem 44 in moving to a closed and non-depressed position. Changing the length of time the motor 26 is energized to move the actuator arm 42 downwardly in block 52 and/or deenergized in the block 54 changes the volume of spray burst released. Thus, the dispenser 34 can be programmed to release any volume of spray burst from the container 36. Modifications to the spray release operation 50 of the present embodiment can include any sequence of the same or different steps, as would be apparent to one of ordinary skill in the art.

The sensor 28 in the present embodiment may be a photocell light sensor. In one embodiment, changes in the detected level of light by the sensor may be construed as detected motion. The sensor 28 may be the sensor described in Carpenter et al. U.S. patent application Ser. No. 11/725,402, which is incorporated herein by reference in its entirety. However, any other type of detector or sensor may be utilized, e.g., a passive infrared or pyroelectric motion sensor, an infrared reflective motion sensor, an ultrasonic motion sensor, or a radar or microwave radio motion sensor. Further, the sensor 28 can be replaced or used in combination with any other type of known sensor, e.g., a heat sensor or an odor sensor. Still further, the sensor does not have to be located within the housing 38 of the dispenser 34; rather, the sensor 28 can be a remote sensor for detecting motion that is not around the dispenser 34.

Figure 4:
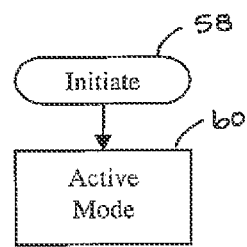
FIG. 4 is a flowchart that illustrates programming that may be executed when a power source is applied to the dispensers of FIGS. 1 and/or 2.

FIG. 4 illustrates an initiation procedure of the dispenser 34. The initiation procedure includes an initiate mode block 58 at which the programming implemented by the microprocessor 22 to control the dispenser 34 initiates when a selector switch 32 is toggled into an on position. Alternatively, if the selector switch 32 is not provided, the initiate mode block 58 may be responsive to the insertion of the batteries 40 into the dispenser 34 or the provision of some other power source to the dispenser 34. After the initiate mode block 58, control passes directly to block 60 without any lockout period therebetween, and an active mode procedure is performed, as will be described in greater detail hereinafter. In other embodiments a startup procedure is performed after the initiate mode 58, following which the active mode procedure 60 is performed. The startup procedure may include any combination of lockout periods and spray release operations, which in some instances may allow the user to determine that the dispenser 34 is functioning properly, e.g., that all of the components are properly coupled together and functioning and that the contents of the container 36 are not depleted. In some embodiments, the sensor 28 may be activated during the initiation procedure 50 and utilized during a startup procedure. Modifications to the programming of the present embodiment can include any sequence of the same or different steps, as would be apparent to one of ordinary skill in the art.

Figure 5:
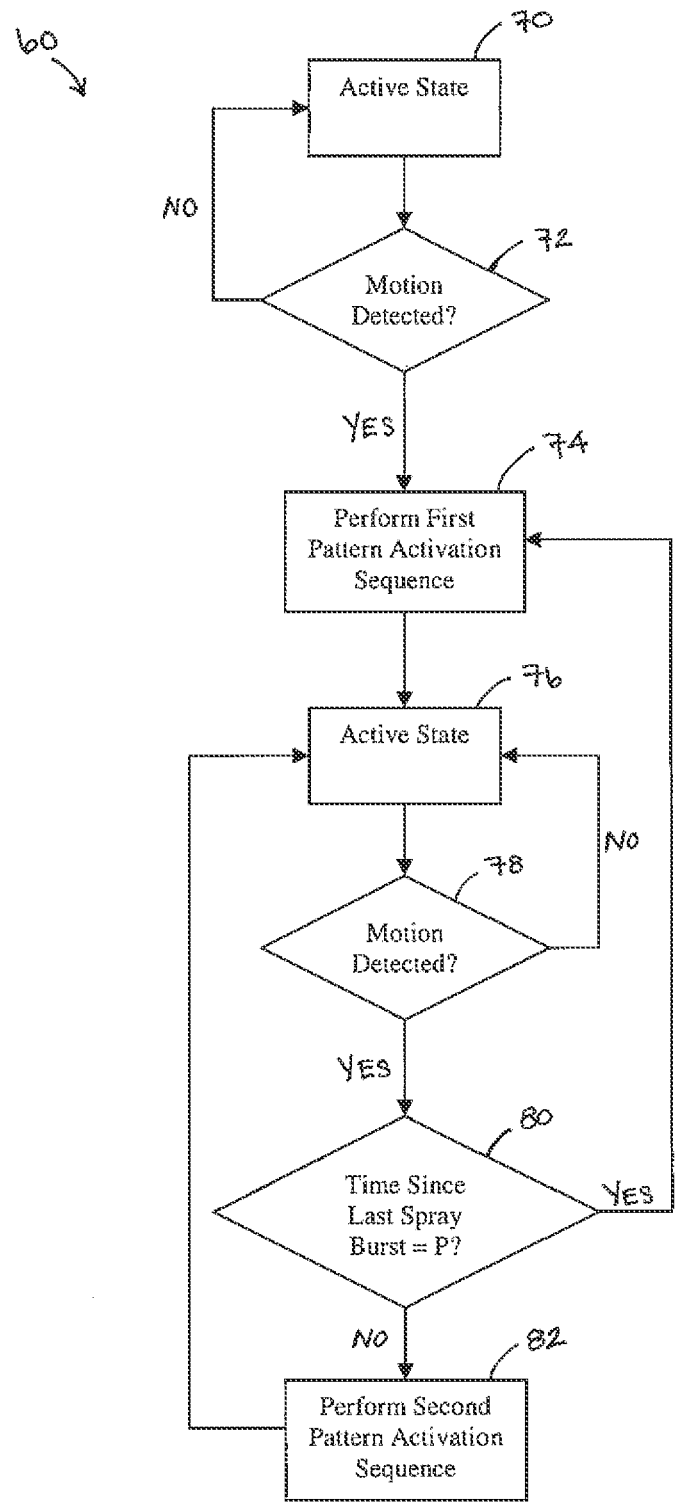
FIG. 5 is a flowchart that illustrates programming that may be executed during an active mode procedure of the dispensers of FIGS. 1 and/or 2.
Figure 6:
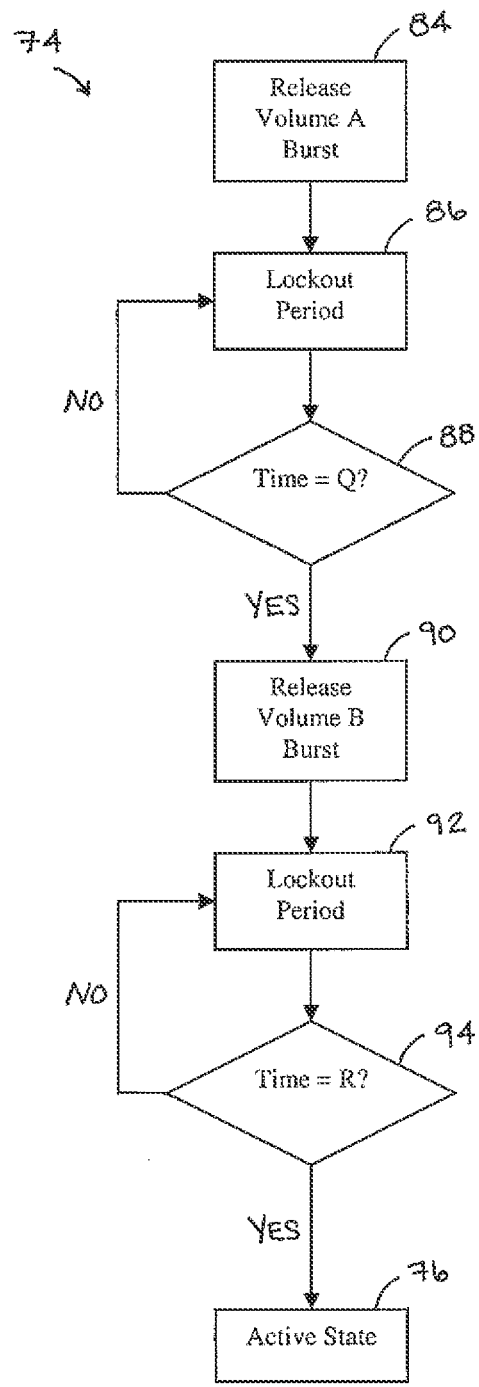
FIG. 6 is a flowchart that illustrates programming that may be executed during a first pattern activation sequence of the programming of FIG. 5.
Figure 7:
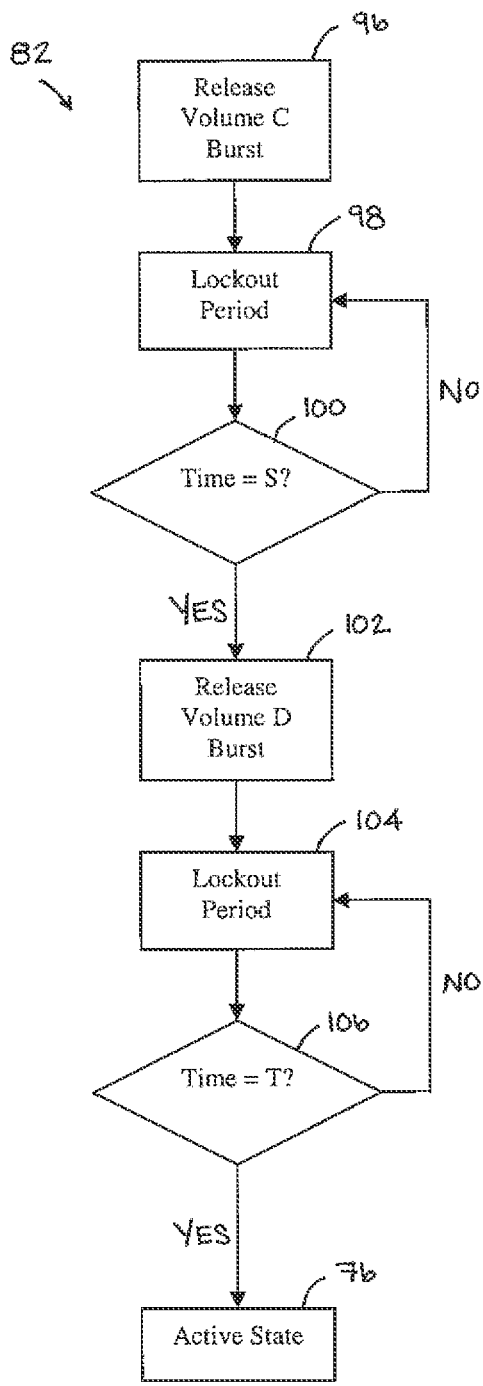
FIG. 7 is a flowchart that illustrates programming that may be executed during a second pattern activation sequence of the programming of FIG. 5.

FIGS. 5-7 illustrate an embodiment of programming executed during the active mode procedure 60. Referring to FIG. 5, at a block 70 the sensor 28 is activated and the dispenser 34 is on and in a first active state. Thereafter, control passes to a decision block 72 to determine if motion is detected. If motion is not detected, control passes back to the block 70 and subsequently proceeds again to the block 72. However, if motion is detected, control passes to a block 74 to perform a first pattern activation sequence. During the first pattern activation sequence 74 the sensor 28 is deactivated, e.g., by ignoring the output from the sensor 28 and/or de-energizing the sensor 28. After performing the first pattern activation sequence 74, control passes to a block 76 in which the dispenser 34 is in a second active state and the sensor 28 is again active. Subsequently, control passes to a decision block 78 to determine if motion is detected. If motion is not detected, control passes back to the block 76 and subsequently proceeds to the block 78. If motion is detected, control passes to another decision block 80 and the programming determines if the time elapsed since the last spray burst has reached a certain time period P. If the time period P has not elapsed control passes to a block 82 to perform a second pattern activation sequence. During the second pattern activation sequence 82 the sensor 28 is again deactivated. After the second pattern activation sequence 82 is performed, control passes back to the block 76 and the device is in the second active state. Referring back to the decision block 80, if the programming determines that the time period P has elapsed then control passes back to the block 74 and the device performs the first pattern activation sequence. Preferably, the time period P since the last spray burst is between about 30 and about 90 minutes. More preferably the time period P is between about 50 and about 70 minutes. Most preferably the time period P is about 60 minutes. Accordingly, other lengths of time for the time period P will be apparent to those skilled in the art.

FIG. 6 illustrates the first pattern activation sequence 74. At a block 84 the dispenser 34 performs a Spray A release operation in which the dispenser releases a volume A burst of material. The spray release operation is similar to the spray release operation 50 described above and illustrated in FIG. 3. The volume A burst of material preferably has a volume between about 10 μL and about 100 μL, more preferably between about 20 μL and about 60 μL, and most preferably between about 30 μL and about 50 μL. It will be apparent to those skilled in the art that a different volume could be used. Thereafter, control passes to a block 86 and the dispenser 34 enters a first lockout period. A decision block 88 determines if the time elapsed during the first lockout period has reached a certain first time Q. In a preferred embodiment the time Q of the first lockout period is between about 5 to about 30 minutes. More preferably, the time Q of the first lockout period is between about 10 to about 20 minutes. Most preferably the time Q is about 15 minutes. If the time elapsed during the first lockout period has not reached the certain first time Q then control loops back to the lockout period of block 86. If the first time Q has elapsed, then control passes to a block 90 and the dispenser 34 performs a Spray B release operation and the dispenser 34 releases a volume B burst. In a preferred embodiment the volume B burst has a volume of 25 μL, but it will be apparent to those skilled in the art that other volumes may be used for the volume B burst. Preferably, the volume B is between about 10 μL and about 100 μL, and more preferably the volume B is between about 20 μL and about 60 μL. While any volume may be released, in a preferred embodiment the volume B burst is less than that of the volume a burst. After releasing the volume B burst the dispenser 34 enters a second lockout period of a block 92. Subsequently control passes to a decision block 94 and the programming determines if the time elapsed during the second lockout period has reached a certain second time R. In a preferred embodiment the second lockout period is between about 1 to about 20 minutes. More preferably the second lockout period is between about 5 to about 10 minutes. Most preferably, the second lockout period is about 10 minutes. If the second lockout period time R has not elapsed control loops back to the second lockout period of block 92. If the second lockout period has elapsed then control loops back to the second active state of block 76 of FIG. 5. In an alternative embodiment the times of the lockout periods and the volumes of material may be changed without departing from the spirit of the invention.

FIG. 7 provides details of the second pattern activation sequence 82. At block 96 the dispenser 34 performs a Spray C release operation in which the dispenser 34 releases a volume C burst. Thereafter, the dispenser 34 enters a third lockout period of block 98. Subsequently, control passes to a decision block 100 and the programming determines if the time elapsed during the third lockout period has reached a certain third lockout time S. If the third lockout period has not elapsed, the control loops back to the third lockout mode of block 98. If the third lockout period S is determined to have elapsed then control passes to a block 102 and the dispenser 34 performs a Spray D release operation and the dispenser releases a volume D burst. The dispenser 34 then enters a fourth lockout mode of block 104. A decision block 106 determines if the time elapsed during the fourth lockout mode has reached a certain fourth lockout period T. If the fourth lockout period T has not elapsed then control loops back to block 104. If the lockout period T has elapsed then control passes back to the second active state of block 76 of FIG. 5. It is preferred that the volume C and the volume D of material are between about 10 μL and about 50 μL. More preferably, the volume C and the volume D of material are between about 20 μL and about 30 μL, with the volume C and the volume D of the most preferred embodiment being about 25 μL. While the volume C and the volume D of material can be different volumes, it is preferred that volume C has the same volume as volume D. The third and fourth lockout periods S, T are preferably between about 5 to about 30 minutes and more preferably between about 10 to about 20 minutes. Most preferably the third and fourth lockout periods S, T are about 10 minutes. Although the third and fourth lockout periods S, T can be different lengths, it is preferred that the third and fourth lockout periods S, T have the same length.

Figure 8:
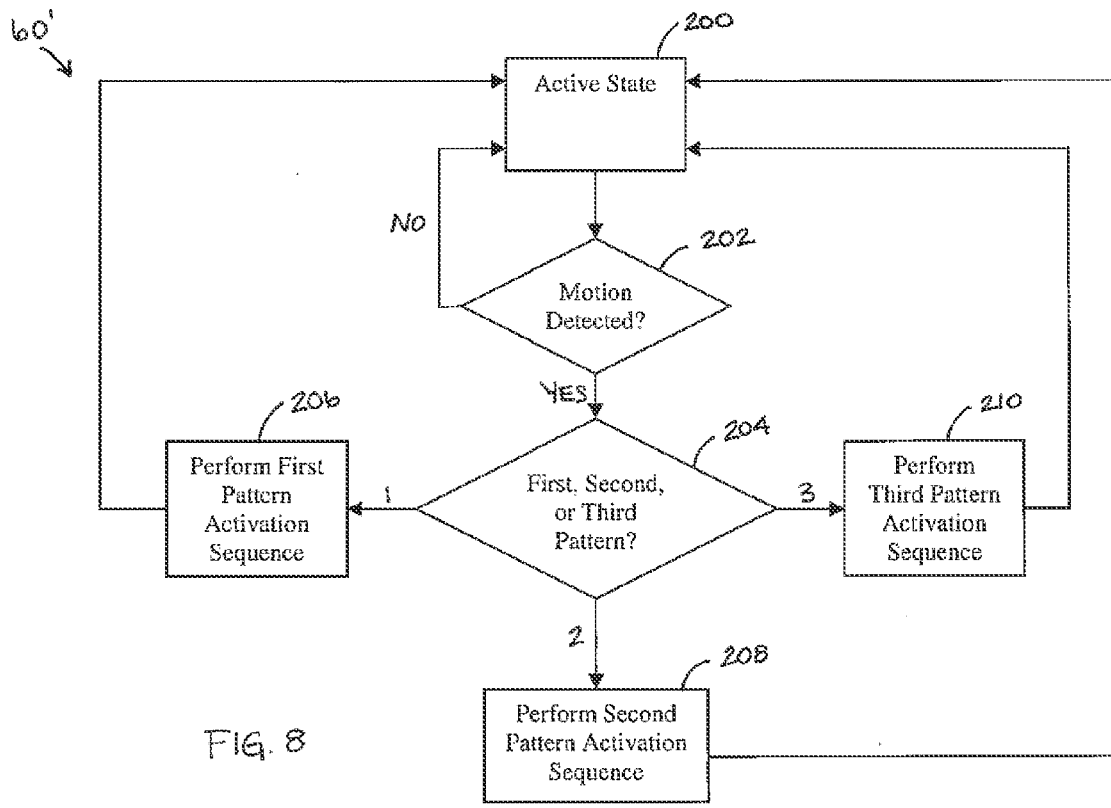
FIG. 8 is a flowchart that illustrates another embodiment of the active mode procedure of the dispensers of FIGS. 1 and/or 2.

FIGS. 8-11 illustrate a second embodiment of programming executed by the dispenser 34 during the active mode procedure 60'. Referring to FIG. 8, at block 200 the sensor 28 is activated and the dispenser 34 is in an active state. Subsequently, control passes to a decision block 202 to determine if motion is detected. If motion is not detected, control loops back to the active state of block 200. If motion is detected, control passes to a second decision block 204 and the programming uses a random number generator to select one of a first, a second, and a third pattern activation sequence represented by blocks 206, 208, and 210, respectively. After performing the first, the second, or the third pattern control loops back to the active state of block 200.

Figures 9, 10, 11:
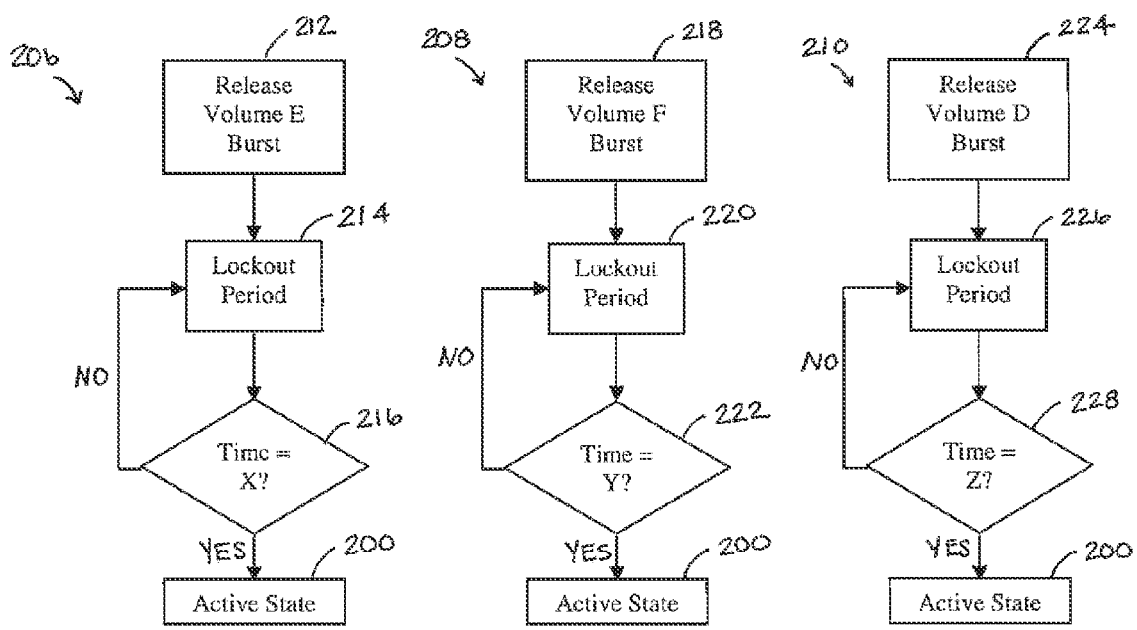
FIG. 9 is a flowchart that illustrates programming that may be executed during a first pattern activation sequence of FIG. 8.
FIG. 10 is a flowchart that illustrates programming that may be executed during a second pattern activation sequence of FIG. 8.
FIG. 11 is a flowchart that illustrates programming that may be executed during a third pattern activation sequence of FIG. 8.

FIGS. 9-11 depict the programming of the first, the second, and the third pattern activation sequences, 206, 208, 210, respectively. In FIG. 9, if the first pattern activation sequence 206 is selected, the sensor 28 is again deactivated and the dispenser 34 performs a Spray E release operation of block 212 and releases a volume E burst of material. The dispenser 34 then enters a first lockout period of block 214. Subsequently, control passes to a decision block 216 and the programming determines if the time elapsed during the first lockout period 214 has reached a certain first time X. If the first time X has not elapsed control loops back to the lockout mode of block 214. If the first time X has elapsed control passes back to the active state of block 200 of FIG. 8.

Referring to FIGS. 10 and 11, the second and third pattern activation sequences 208, 210 are programmed similarly to the first pattern activation sequence 206, except for changes in the volume of the spray bursts released and the length of time of the lockout periods. As shown in FIG. 10, the second pattern activation sequence 208 releases a volume F burst at a block 218 and enters a second lockout period 220 where the second lockout time of block 222 is Y. FIG. 11 shows the third pattern activation sequence 210. At block 224 the dispenser 34 releases a volume G burst and subsequently enters a third lockout period of block 226 where the third lockout time of block 228 is Z.

In the second embodiment the volume E, the volume F, and the volume G of material are preferably between about 10 μL and about 100 μL. More preferably the volumes E, F, and G are between about 15 μL and about 60 μL, where the most preferred volumes E, F, and G are between about 20 μL and about 50 μL. The volumes E, F, and G can all be the same volume, but it is preferred that volumes E, F, and G are different. The first, second, and third lockout periods X, Y, Z of the second embodiment preferably last about 5 to about 30 minutes. More preferably the first, second, and third lockout periods X, Y, Z last about 10 to about 25 minutes, and most preferably about 10 to about 20 minutes. While it is contemplated that the first, second, and third lockout periods X, Y, Z of the second embodiment can last the same length of time, it is preferred that the first, second, and third lockout periods X, Y, Z are different.

In a different embodiment similar to those described above, any of the active dispensers 34 may also be provided with passive diffusion means. In addition to actively releasing a spray burst upon the detection of motion, this embodiment also provides a continual passive diffusion of a volatile material. The passive diffusion means may comprise a reservoir holding a fragrance ladened liquid or gel enclosed by a vapor permeable membrane. As ambient air passes over the reservoir, the fragrance permeates through the membrane and is slowly diffused into the atmosphere. The reservoir may be attached to the outside of the housing 38 or recessed in some manner within the housing 38 of the dispenser 34. The passive diffusion means slowly diffuses the fragrance into the atmosphere, providing a low level of fragrance between the high levels of fragrance released during the active spray bursts.

In yet another embodiment similar to those described above, the dispenser 34 emits two spray bursts as opposed to a single burst when activated in response to a sensor or predetermined emission pattern. The first spray burst is released into the atmosphere in a manner as noted above. The second spray burst is sprayed onto an emanating pad located within the dispenser 34. The emanating pad absorbs the volatile material sprayed onto it and allows for the continual diffusion of the volatile material from the emanating pad into the atmosphere.

It is contemplated that other types of dispensers with varying actuation mechanics may be used in conjunction with any of the embodiments disclosed herein. For example, instead of using a dispenser capable of releasing spray bursts of various volumes from a single container it is possible to use a dispenser capable of releasing spray bursts from multiple containers with differently metered valves. Also, instead of using a dispenser that uses a container with a metered valve, it is possible to use a dispenser that uses submetered valves, in which the submetering happens within the dispenser and not within the container. For example, it is contemplated that the dispenser may use an electronically controlled solenoid in combination with a container having a non-metered or metered valve to release various volumes of spray material from the dispenser.

It is further contemplated that any of the described dispensers could use a remote sensor as opposed to the sensor 28 located within the housing of the dispenser. Remote sensors have the advantage of allowing the dispenser 34 to detect motion that is not in the same location as the dispenser 34 or to increase the range of detection. Additionally, any of the described dispensers may use multiple sensors, located within or outside of the dispenser 34, to equip the dispenser with omni-directional detection capabilities.

It is also imagined that any of the above embodiments may be modified to include a user selectable switch. The user selectable switch allows a user to choose a preferred lockout period time for any of the lockout periods. In one example, the user can select one of a level 1, a level 2, a level 3, and a level 4 lockout period, wherein level 1 is about 40 minutes, level 2 is about 31.6 minutes, level three is about 23.3 minutes, and level 4 is about 15 minutes. It is understood that the switch can have more or less choices of lockout period times for the user to select. Alternatively, instead of a switch, the dispenser could include a wheel or a dial, which the user can turn to select a preferred lockout period time or times.

Various modifications can be made to the above embodiments without departing from the spirit of the present disclosure. For example, the volumes of the spray bursts A, B, C, D, E, F, and G may be changed. Additionally the time elapsed during the lockout periods P, Q, R, S, T, X, Y, and Z may be changed without departing from the spirit of the present disclosure. Further, other embodiments of the disclosure including all the possible different and various combinations of the individual features of each of the foregoing described embodiments are specifically included herein.

INDUSTRIAL APPLICABILITY

The dispenser and programming methods described herein advantageously allow for the contents of a container to be sprayed into the atmosphere in a manner that will increase user perception and prevent habituation.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of operating a dispensing device, comprising the steps of:
    entering a first active state,
    detecting a sensory input by a sensor,
    initiating a first pattern activation sequence configured to energize a drive unit of the dispensing device for a first length of time to actuate a container,
    entering a second active state upon completion of the first pattern activation sequence, and
    detecting a second sensory input in the second active state,
    wherein if the second sensory input is detected before a lapse of time period P, the method comprises the steps of:

initiating a second pattern activation sequence configured to energize the drive unit for a third length of time to actuate a container, and
wherein if the second sensory input is detected after a lapse of time period P, the method comprises the steps of:
initiating the first pattern activation sequence;
wherein at least one of the following method steps occurs within the first or the second active state:
(i) energizing the drive unit for a second length of time subsequent to the first length of time; or
(ii) energizing the drive unit for a fourth length of time subsequent to the third length of time;
wherein the first, second, third and fourth lengths of time are not all the same.

2. A method of operating a dispensing device, comprising the steps of:
entering a first active state, wherein if there is sensory input detected by a sensor of the dispensing device the following steps are taken:
detecting the sensory input;
initiating a first pattern activation sequence comprising the release of a volume A of material from a fluid container; and
entering a second active state upon completion of the first pattern activation sequence, wherein if there is sensory input detected by a sensor of the dispensing device before the lapsing of a time period P, the following steps are taken:
detecting the sensory input;
initiating a second pattern activation sequence comprising the release of a volume C of material from a container,
wherein at least one of the following occurs within the first or second active state:
(i) a volume B of material is released from the container subsequent to the release of the volume A; or
(ii) a volume D of material is released from the container subsequent to the release of the volume C,
wherein volumes A, B, C, and D are not all the same, and
wherein upon entering the second active state, if there is no sensory input detected by a sensor of the dispensing device before the lapsing of a time period P, the following steps are taken:
initiating the first pattern activation sequence.

3. The method of claim 2, wherein the first pattern activation sequence includes at least one lockout period between at least one of the release of the volume A and the volume B and between the release of the volume B and the entering of the second active state.

4. The method of claim 3, wherein the at least one lockout period is between about 1 to about 30 minutes.

5. The method of claim 2, wherein at least one of the volume A, the volume B, the volume C, and the volume D is between about 10 μL to about 100 μL.

6. The method of claim 2, wherein the second pattern activation sequence includes at least one lockout period between at least one of the release of the volume C and the volume D and between the release of the volume D and the entering of a second active state.

7. The method of claim 2, wherein the volume A, volume B, volume C, and volume D are released from a single fluid container.

8. The method of claim 2, wherein the volume A, volume B, volume C, and volume D are released from multiple fluid containers.

9. The method of claim 2, wherein the sensor is at least one of a heat sensor, an odor sensor, a vibration sensor, a tilt sensor, a sound sensor, a water level sensor, a pressure sensor, a humidity sensor, a temperature sensor, and a motion sensor.

10. The method of claim 2, wherein the sensor is a remote sensor.

11. The method of claim 2, wherein a volume B is released from the container subsequent to the release of the volume A in the first active state and the volume D is released from the container subsequent to the release of the volume C in the second active state.

12. A method of operating a dispensing device, comprising the steps of:
entering a first active state,
detecting a sensory input by a sensor,
initiating a first pattern activation sequence configured to energize a drive unit of the dispensing device for a first length of time and a second subsequent length of time to actuate a container,
entering a second active state upon completion of the first pattern activation sequence, and
detecting a second sensory input in the second active state,
wherein if the second sensory input is detected before a lapse of time period P, the method comprises the steps of:
initiating a second pattern activation configured to energize the drive unit for a third length of time and a fourth subsequent length of time to actuate a container, and
wherein if the second sensory input is detected after a lapse of time period P, the method comprises the steps of:
initiating the first pattern activation sequence;
wherein the first, second, third, and fourth lengths of time are not all the same.

13. The method of claim 12, wherein the drive unit is a motor.

14. The method of claim 12, wherein the dispensing device includes at least one lockout period between the first length of time, the second length of time, the third length of time, and the fourth length of time.

15. The method of claim 12, wherein a single container is actuated in the first, the second, the third, and the fourth lengths of time.

16. The method of claim 12, wherein multiple containers are actuated in the first, the second, the third, and the fourth lengths of time.

17. The method of claim 12, wherein the sensor is a motion sensor.

18. The method of claim 17, wherein the motion sensor comprises at least one of a photocell motion sensor, a passive infrared motion sensor, a pyroelectric motion sensor, an infrared reflective motion sensor, an ultrasonic motion sensor, a radar motion sensor, or a microwave radio sensor.

19. The method of claim 12, wherein the sensor is at least one of a heat sensor, an odor sensor, a vibration sensor, a tilt sensor, a sound sensor, a water level sensor, a pressure sensor, a humidity sensor, and a temperature sensor.

* * * * *